United States Patent
Koike et al.

(10) Patent No.: US 6,240,784 B1
(45) Date of Patent: Jun. 5, 2001

(54) STRESS EVALUATION METHOD AND APPARATUS THEREFOR

(75) Inventors: Masahiro Koike, Hitachi; Fuminobu Takahashi, Katsuta; Hideki Inoue, Hitachi; Yosinori Musha, Hitachioota; Shuuji Kamimoto, Hitachi; Shinji Naito, Hitachioota; Tsukasa Sasaki, Hitachi, all of (JP)

(73) Assignee: Hitachi, Ltd., Tokyo (JP)

( * ) Notice: Subject to any disclaimer, the term of this patent is extended or adjusted under 35 U.S.C. 154(b) by 879 days.

(21) Appl. No.: 08/715,221

(22) Filed: Sep. 17, 1996

Related U.S. Application Data

(63) Continuation of application No. 08/313,840, filed on Sep. 28, 1994, now Pat. No. 5,557,048.

(30) Foreign Application Priority Data

Sep. 28, 1993 (JP) .................................................. 5-240936

(51) Int. Cl.⁷ .................................................. G01N 29/18
(52) U.S. Cl. .................................................. 73/597; 73/794
(58) Field of Search ............................. 73/597, 794, 761, 73/786, 788

(56) References Cited

U.S. PATENT DOCUMENTS

| | | | |
|---|---|---|---|
| 3,986,391 | * 10/1976 | Vahaviolos | 73/781 |
| 4,033,182 | * 7/1977 | Clotfelter | 73/597 |
| 4,056,970 | * 11/1977 | Sollish | 73/597 |
| 4,080,836 | * 3/1978 | Thompson et al. | 73/643 |
| 4,121,467 | * 10/1978 | Gerhart | 73/597 |
| 4,210,028 | * 7/1980 | Hildebrand | 73/598 |
| 4,364,114 | * 12/1982 | Renzel et al. | 73/597 |
| 4,399,702 | * 8/1983 | Suzuki | 73/597 |
| 4,413,517 | * 11/1983 | Soden | 73/597 |
| 4,569,229 | * 2/1986 | de Halleux | 73/597 |
| 4,995,260 | * 2/1991 | Deason et al. | 73/632 |
| 5,125,273 | * 6/1992 | Negita | 73/597 |
| 5,154,081 | * 10/1992 | Thompson et al. | 73/597 |
| 5,307,680 | * 5/1994 | Drescher-Krasicka | 73/606 |
| 5,341,683 | * 8/1994 | Searle | 73/610 |

FOREIGN PATENT DOCUMENTS

| | | |
|---|---|---|
| 54-158284 | 12/1979 | (JP) . |
| 56-90228 | 7/1981 | (JP) . |
| 61-254849 | 11/1986 | (JP) . |
| 5-18833 | 1/1993 | (JP) . |

* cited by examiner

*Primary Examiner*—Eric S. McCall
(74) *Attorney, Agent, or Firm*—Antonelli, Terry, Stout & Kraus, LLP

(57) ABSTRACT

A stress evaluation method for evaluating stress acting on a test piece includes the steps of transmitting acoustic waves including a surface wave, a longitudinal wave, and a shear wave through the test piece; receiving the acoustic waves after they have propagated through the test piece; obtaining acoustic velocities of the surface wave at a non-loaded portion and a loaded portion of the test piece based on the received acoustic waves; evaluating a stress in a surface layer of the test piece based on a difference between the surface wave acoustic velocities at the non-loaded portion and the loaded portion and a predetermined relationship between surface wave acoustic velocities and stresses; obtaining an acoustic velocity of the longitudinal wave at the non-loaded portion based on the received acoustic waves; calculating an acoustic velocity of the shear wave at the loaded portion based on the received acoustic waves and the longitudinal wave acoustic velocity at the non-loaded portion; evaluating an internal average stress in the test piece based on the shear wave acoustic velocity at the loaded portion; evaluating an internal stress distribution in the test piece by correcting a hypothetical internal stress distribution in the test piece based on the stress in the surface layer and the internal average stress; and conducting a diagnosis of the test piece based on the internal stress distribution.

10 Claims, 16 Drawing Sheets

STRESS EVALUATION METHOD AND APPARATUS THEREFOR

CROSS-REFERENCE TO RELATED APPLICATION

This is a continuation of application Ser. No. 08/313,840 filed on Sep. 28, 1994, now U.S. Pat. No. 5,557,048.

BACKGROUND OF THE INVENTION

The present invention relates to a stress evaluation method using acoustic waves and an apparatus therefor which is capable of evaluating stress acting on a test piece under inspection.

It is well known to use acoustic waves to obtain a magnitude of stress acting on the test piece on the basis of changes in acoustic velocity.

Namely, according to a prior art method which uses a relationship obtained in advance between a ratio of changes in acoustic velocity and stress values, a magnitude of stress acting on a particular point can be obtained from the acoustic velocity measured at that point.

The stress evaluation method using a surface wave for evaluating stress present in the surface layer of the test piece has been disclosed, for example, in JP-A-61-254849.

Further, there is a method to obtain a measure of internal stress in the test piece as an average value from a difference in acoustic velocities between a shear wave which oscillates in the parallel direction relative to the stress and a shear wave which oscillates in the orthogonal direction relative to the stress, as disclosed in JP-A-56-90228.

SUMMARY OF THE INVENTION

In the prior art methods described above, however, no particular attention has been paid to the fact that an acoustic velocity will change depending on the texture orientation of the test piece.

Further, in the case where the thickness of the test piece is unknown, it is necessary to obtain acoustic velocities of two kinds of shear waves by changing their oscillating directions relative to each other, and, consequently, to obtain stress from a slight difference between these two acoustic velocities. Therefore, it has been difficult to improve the precision of detection, and in addition, the stress value thus obtained merely indicates an average stress in the thickness direction, without regard to the stress distribution.

A main object of the invention is to improve the precision of stress evaluation of a test piece on the basis of changes in acoustic velocity.

Another object of the invention is to facilitate usage of a stress evaluation method having an improved precision.

A first aspect for accomplishing the main object of the invention provides for a method for implementing evaluation of the stress acting on a test piece on the basis of changes in acoustic velocity of a sound which propagates through the test piece, the method comprising the steps of modifying the propagational direction of a surface wave propagating through the surface layer of the test piece between a non-loaded portion and a loaded portion therein, measuring the acoustic velocity of said surface wave, and evaluating a surface stress in the loaded portion of the test piece from a difference in the acoustic velocities of the surface wave between the non-loaded and loaded portions of the test piece. A second aspect of the invention likewise provides a stress evaluation method comprising the steps of causing a longitudinal wave and a shear wave to be propagated in the loaded portion in the thickness direction thereof, obtaining respective propagation times for the longitudinal wave and the shear wave in the test piece upon reception of reflected waves from the bottom surface of the test piece in the thickness direction, calculating the thickness at the loaded portion from the longitudinal wave acoustic velocity at the non-loaded portion, which has been obtained according to a ratio between the calculated thickness and the propagation time, evaluating the shear wave acoustic velocity from the calculated thickness and the propagation time of the shear wave at the loaded portion, and evaluating the magnitude of the internal average stress exerted in the thickness direction inside the loaded portion. A third aspect of the invention likewise provides a stress evaluation method comprising the steps of correcting a hypothetical stress distribution in the thickness direction in the test piece such that, in the hypothetical stress distribution in the thickness direction of the test piece which was predetermined, the surface stress in the test piece is corrected by a surface stress value which has been evaluated according to the first aspect described above, and the average stress of the stress distribution in the thickness direction likewise is corrected by an internal average stress value which has been evaluated by the second aspect described above, so as to establish a correct internal stress distribution in the thickness direction of the test piece. A fourth aspect for accomplishing still another object of the invention provides for a plant diagnosis method comprising the steps of evaluating the stress in a test piece through the stress evaluation method according to the first aspect or the third aspect of the invention, and interrupting the operation of equipment including the above test piece or the plant if a value of the stress which has been evaluated becomes greater than an allowable stress value which has been predetermined. Likewise, a fifth aspect of the invention provides for a plant diagnosis method comprising the steps of repeating a stress evaluation if the stress value evaluated according to the fourth aspect described above is smaller than the predetermined allowable stress value, and classifying modes of material degradation in the test piece based on time variations of the evaluated stress values. Likewise, a sixth aspect of the invention provides for a welding procedure management method comprising the steps of evaluating a residual stress in a test piece subjected to an initial welding and heat treatment by means of the stress evaluation method of the first aspect or the third aspect of the invention, and applying a subsequent welding and heat treatment to the test piece in the case when the residual stress evaluated above is greater than a predetermined allowable stress value. Likewise, a seventh aspect of the invention provides for a welding procedure management method comprising the step of providing the same conditions as the initial welding and heat treatment conditions for a subsequent rewelding and heat treatment carried out after employing the sixth aspect of the invention. Likewise, an eighth aspect of the invention provides for a welding procedure management method comprising the steps of reevaluating a residual stress in the test piece subjected to rewelding and heat treatment in accordance with the seventh aspect by means of a stress evaluation method according to the first aspect or the third aspect, applying another welding and heat treatment to the test piece after the reevaluation by modifying the welding and heat treatment conditions to be different from the initial conditions, if the residual stress reevaluated above is greater than the foregoing predetermined allowable value, and executing still another reevaluation thereof. Likewise, a ninth aspect of the invention provides for still another welding procedure management method according to the sixth aspect further comprising the step of modifying the welding and heat treatment conditions to be different from the initial welding and heat treatment conditions. A tenth aspect for accomplishing the main object of the invention provides for stress evaluation equipment which is provided with means for propagating an acoustic wave through a test piece, means for receiving the acoustic wave propagated through the test piece, and means for evaluating stress in the test piece on the basis of a signal received by the receiving means and from a variation of the acoustic velocity of the acoustic wave which has propagated through the test piece, wherein the stress evaluation equipment comprises acoustic wave propagational direction varying means for varying at a non-loaded portion and a loaded portion of the test piece the propagational direction of a surface wave which propagates through the surface layer of the test piece, measuring means for measuring the acoustic velocity of each surface wave described above, and evaluation means for evaluating stress at the loaded portion of the test piece from a difference in the acoustic velocities of respective surface waves at the non-loaded portion and the loaded portion of the test piece. Likewise, an eleventh aspect of the invention provides for stress evaluation equipment comprising acoustic wave propagation means for propagating a longitudinal wave and a shear wave through a test piece in a thickness direction at a loaded portion of the test piece, receiving means for receiving respective reflected waves thereof, propagation time measuring means for measuring the propagation times of the longitudinal wave and the shear wave through the test piece in the thickness direction thereof after reception of the reflected waves reflected from the bottom surface of the test piece, longitudinal wave acoustic velocity calculating means for obtaining a longitudinal wave acoustic velocity at the non-loaded portion from a ratio between said thickness and said propagation time, thickness calculating means for calculating a thickness at said loaded portion on the basis of the longitudinal wave acoustic velocity obtained by the above longitudinal wave acoustic velocity calculating means, shear wave acoustic velocity calculating means for obtaining a shear wave acoustic velocity of the shear wave which propagated therethrough from a relation between the thickness obtained by the thickness calculating means and the shear wave propagation time at the loaded portion obtained by the foregoing measuring means, and evaluation means for calculating an average stress magnitude in the thickness direction acting inside the loaded portion of the test piece from the shear wave acoustic velocity obtained by the shear wave acoustic velocity calculating means and on the basis of a relationship between the shear wave acoustic velocity and the stress which was obtained in advance.

According to the first aspect and the tenth aspect described above, an effect due to a texture orientation in the test piece can be avoided by arranging the propagational direction of a surface wave propagating in the surface layer of the test piece such that it is varied at the non-loaded portion and the loaded portion thereof, for example, from 0° to 180°, and that the acoustic velocities thereof are measured, following which a magnitude of stress is evaluated based on a difference between the measured acoustic velocities.

According to the second aspect and the eleventh aspect described above, an average stress in the thickness direction can be obtained by first obtaining the thickness of a test piece by use of a longitudinal wave having an acoustic velocity which changes little due to stress, and then a shear wave acoustic velocity which is sensitive to stress is obtained from a relationship between the thickness obtained above and a shear wave propagation time obtained at the loaded portion.

According to the third aspect of the invention, a stress distribution in the thickness direction is evaluated by correcting a hypothetical stress distribution in the thickness direction presumed in advance such that its surface stress value is corrected by a measured stress value in the surface layer, and its internal average stress value is corrected by a measured internal average stress value.

According to the fourth aspect of the invention, it is possible to provide a plant diagnosis capability which can identify precisely any of the plant stop conditions on the basis of a result of evaluation according to the third aspect.

According to the fifth aspect of the invention, it is possible to classify modes of material degradation in the test piece from time-series evaluation information thereof in addition to carrying out the procedures according to the fourth aspect.

According to the sixth aspect of the invention, through evaluation of residual stress after welding in a welded portion of the test piece by the stress evaluation method according to the first aspect or the third aspect, and through comparison with a predetermined allowable stress value, the quality and reliability of the welded portion is evaluated and a decision is made as to whether or not a rewelding and heat treatment is required to ensure the reliability of the welded portion.

According to the seventh aspect, in addition to the procedures of the sixth aspect, since the initial welding and heat treatment conditions are normally set at their best conditions, rewelding and heat treatment conditions are set so as to be the same as the initial best conditions so as to ensure the reliability of the welded portion to be attained by subsequent rewelding and heat treatment under the best available conditions.

According to the eighth aspect of the invention, in addition to the procedures of the seventh aspect, a procedure for ensuring the reliability of the welded portion is provided by modifying the welding and heat treatment conditions after reevaluation thereof.

Further, according to the ninth aspect of the invention, in addition to the procedures of the sixth aspect, a procedure for ensuring the reliability of the welded portion to be attained is provided by modifying rewelding and heat treatment conditions.

BRIEF DESCRIPTION OF THE DRAWINGS

The invention will be more particularly described with reference to the accompanying drawings, in which.

DESCRIPTION OF THE PREFERRED EMBODIMENTS

Preferred embodiments of the present invention will now be described with reference to the accompanying drawings.

Figure 1:
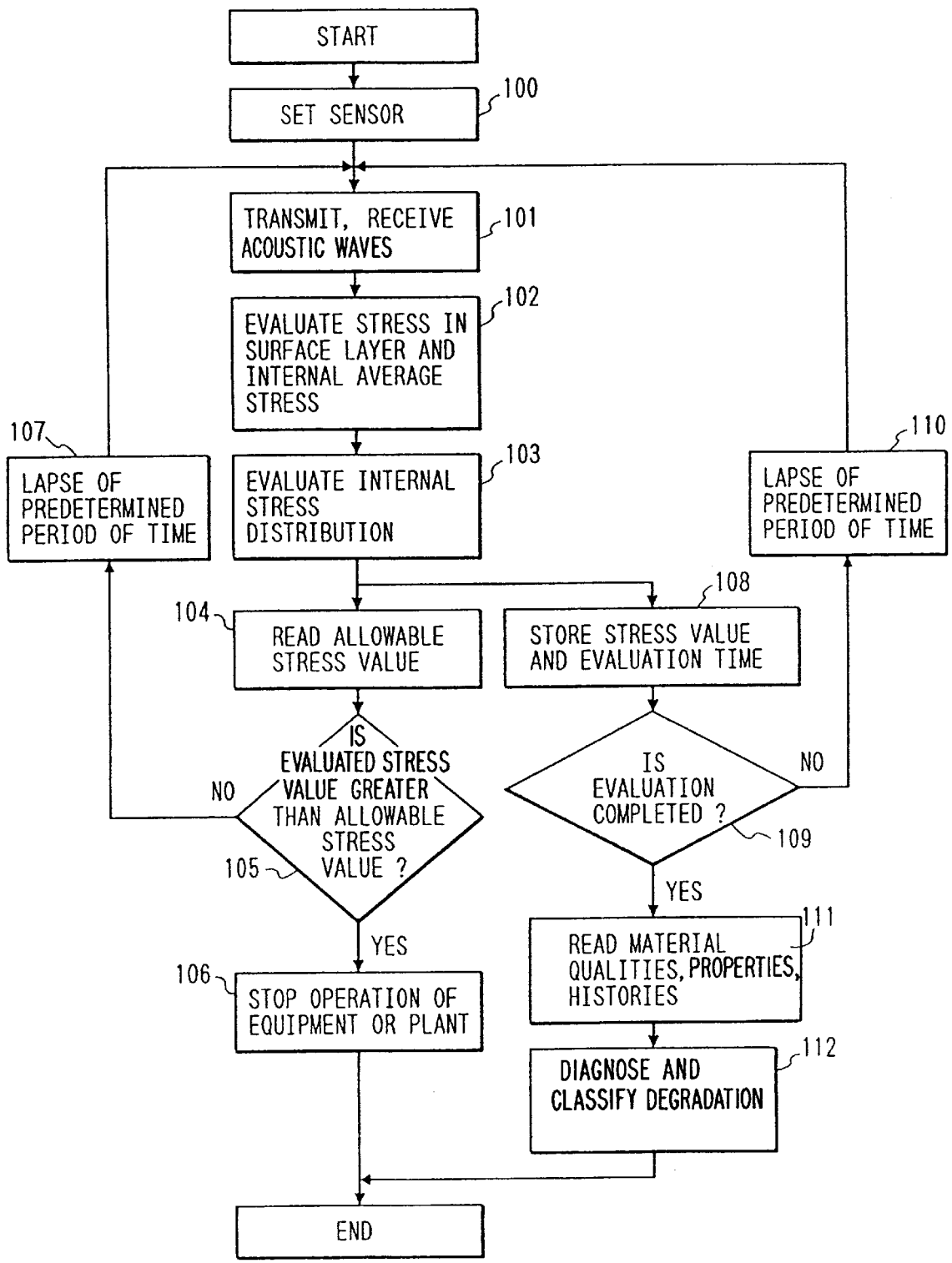
FIG. 1 is a flow chart illustrating a plant diagnosis method of an embodiment according to the invention.

FIG. 1 is a flow chart illustrative of an example of a plant diagnosis method using a stress evaluation method of the invention.

After placing a sensor which transmits and receives acoustic waves including a surface wave, a longitudinal wave, and a shear wave at a target position (step 100 in FIG. 1), transmission and reception of the acoustic waves are carried out (step 101).

Then, a surface layer stress and an internal average stress are evaluated based on the acoustic velocities of the received acoustic waves (step 102), after which a precise internal stress distribution is evaluated by correcting a hypothetical internal stress distribution using the surface layer stress and the internal average stress evaluated above (step 103).

Then, the subsequent steps are divided into two paths. One path is for diagnosing the normal condition of equipment or a plant by at least one stress evaluation processing, and the other path is for storing evaluated stress values and diagnosing the reliability of the equipment or plant from time variations of the stored evaluated stress values.

In the former path, an allowable stress value which has been predetermined based on data on material strength, design margins and the like and stored in memory is read out (step 104).

The evaluated stress value is compared with the allowable stress value (step 105), and if the evaluated stress value is larger than the allowable value, an abnormality of the equipment or plant is judged to be present, and therefore the equipment or plant is shut down (step 106).

If the evaluated value is smaller than the allowable stress value, the equipment or plant is judged to be normal. Then, after elapse of a predetermined period of time (step 107), a subsequent stress evaluation is carried out again through transmission and reception of acoustic waves.

Namely, the steps beginning with step 101 are repeated. On the other hand, the latter path includes the following steps.

The evaluated stress value and its corresponding time of evaluation are stored in memory (step 108).

Upon verifying that the equipment or plant is operating normally, it is judged whether the evaluation is completed or not (step 109).

If the evaluation is judged not to be completed, the steps beginning with step 101 are carried out upon elapse of a predetermined period of time (step 110).

When the operation of the equipment or plant is interrupted, by reading out a prestored quality, property and history of a corresponding material at its respective points of measurements (step 111), a diagnosis of material degradation and its classification are conducted (step 112).

For example, a creep phenomenon, which is one type of material degradation, occurs when a constant load (stress) is applied to a test piece subjected to a high temperature environment, whereas fatigue occurs when a variable load (stress) is applied thereto under a high temperature.

Therefore, it is possible to know whether a constant stress has acted on the test piece or a variable stress has acted thereon from time variations of the evaluated stress values stored in step 108, thereby enabling diagnosis and classification of a specific material degradation.

Figure 2:
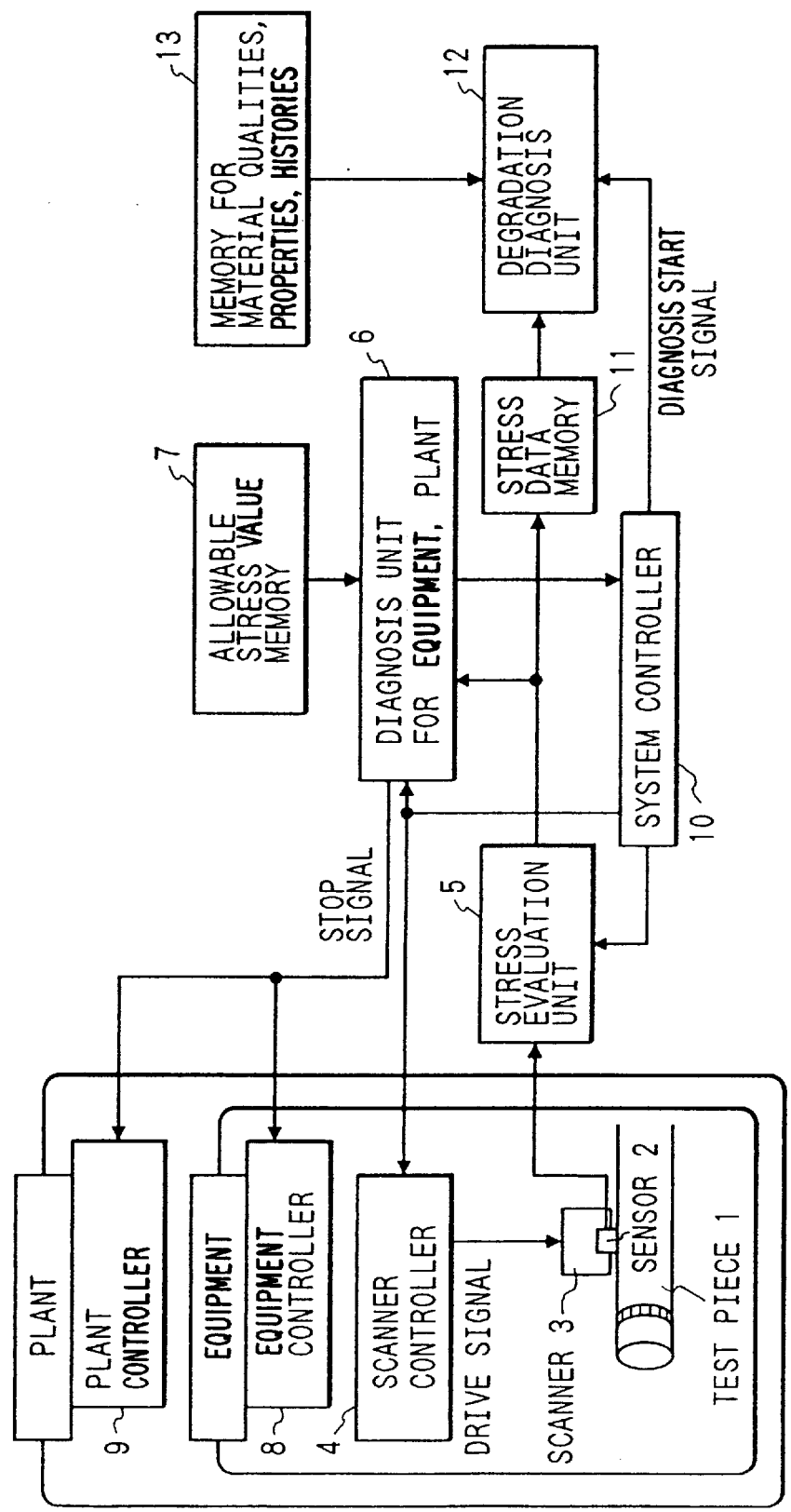
FIG. 2 is a schematic system diagram illustrative of an equipment configuration for implementing the plant diagnosis method of FIG. 1.

FIG. 2 is a schematic block diagram illustrating an example of an equipment configuration for implementing the plant diagnosis method of FIG. 1. In FIG. 2, numeral 1 designates a test piece of piping for use in a power generation plant or the like.

A scanner 3 is moved in response to a drive signal from a scanner controller 4 such that a sensor 2 which transmits and receives acoustic waves including a surface wave, a shear wave, and a longitudinal wave is placed at a target position on the test piece 1.

The sensor 2 transmits and receives acoustic waves, and acoustic wave signals corresponding to the received acoustic waves are sent to a stress evaluation unit 5 which evaluates a surface layer stress, an internal average stress and an internal stress distribution based on the acoustic wave signals.

The evaluated stress values are transmitted to an equipment/plant diagnosis unit 6 and a stress data memory unit 11.

The equipment/plant diagnosis unit 6 reads out allowable stress values stored in an allowable stress value memory 7, and compares the evaluated stress values with the allowable stress value in order to verify the reliability of the equipment and/or plant.

If an abnormality is judged to be present, a stop signal is issued and transmitted to an equipment controller 8 and/or a plant controller 9 so as to stop the operation of the equipment and/or plant.

If no abnormality is judged to be present, assuring the reliability of the equipment and/or plant, a system controller 10 is caused to issue an instruction to the stress evaluation unit 5 to carry out stress evaluation after elapse of a predetermined period of time.

A stress data memory 11 then stores the stress values thus evaluated and a corresponding time of their evaluation.

The system controller 10 further verifies that the equipment and/or plant is operating normally, and judges whether or not the evaluation step should proceed.

If the equipment and/or plant are shut down, the system controller 10 issues a diagnosis start signal to a degradation diagnosis unit 12.

The degradation diagnosis unit 12 reads out data on the quality, property and history of material of the test piece stored in a material quality/property/history memory 13, and then carries out degradation diagnosis and its classification.

Figure 3:
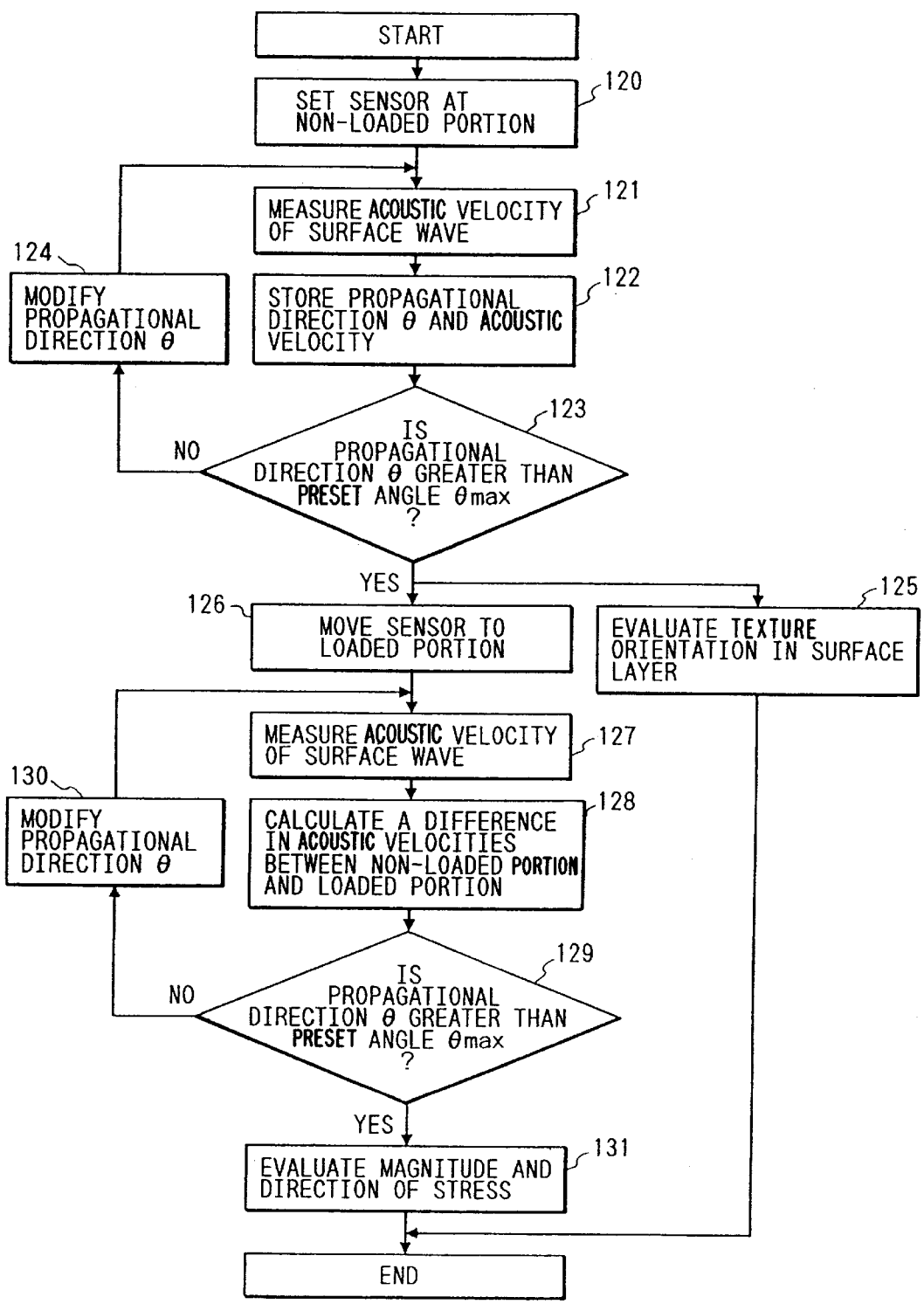
FIG. 3 is a flow chart of a stress evaluation method of FIG. 1 for evaluating stress in the surface layer of a test piece.

With reference to FIG. 3, an example of a stress evaluation method is shown for evaluating surface layer stress in the test piece 1 in regard to step 102 in FIG. 1.

The sensor 2 for transmitting and receiving a surface wave is placed at a position in a non-loaded portion of the test piece (step 120 in FIG. 3).

Then, a surface wave which propagates in the surface layer of the test piece is transmitted and received, and the acoustic velocity of the surface wave is measured (step 121). Then, a propagational direction θ of the surface wave and its acoustic velocity are stored (step 122).

Upon comparison of the propagational direction θ of the surface wave with a preset angle $\theta_{max}$ (step 123), if the propagational direction θ is smaller than the preset angle $\theta_{max}$, the propagational direction of the surface wave is varied (step 124), and then the acoustic velocity of the surface wave is measured again.

If the propagational direction θ is larger than the preset angle $\theta_{max}$, the subsequent steps are divided into two paths: a stress evaluation path and a texture orientation evaluation path.

Figure 5:
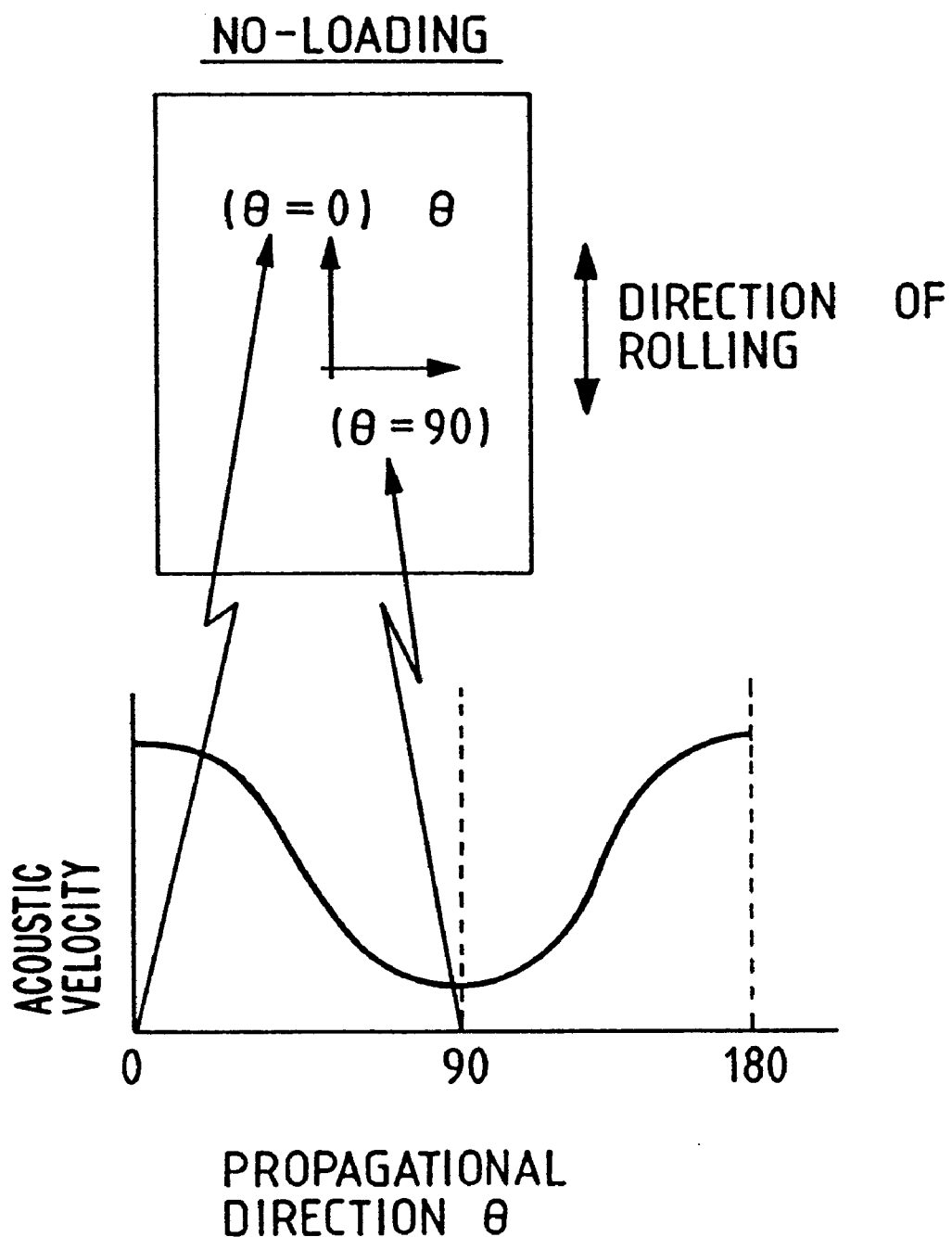
FIG. 5 is a schematic diagram showing a relationship between the angle of a propagational direction of a surface wave, which is formed with a direction of a texture of the surface layer, and an acoustic velocity change.

As shown in FIG. 5, the acoustic velocity of a surface wave in a rolled material, for example, varies with respect to an angle θ formed between its propagational direction and a rolling direction.

Figure 16:
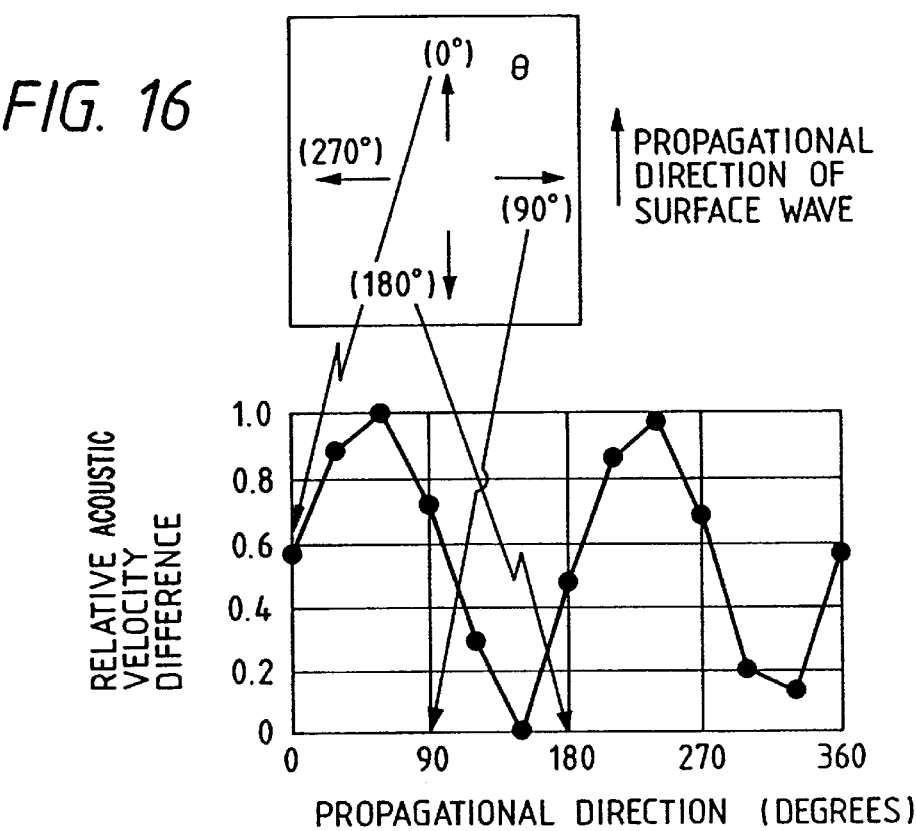
FIG. 16 is a diagram showing a result of experiments with a high tensile steel wherein acoustic velocity changes are plotted relative to propagational directions of a surface wave.

With reference to FIG. 16, there is shown a result of variations of acoustic velocity actually obtained for stainless steel by changing the propagational direction θ of a surface wave from 0° to 360°. It can be seen that the acoustic velocity changes cyclically with a period of 180°.

Now, back to FIG. 3, in step 125 of the texture orientation evaluation, a texture orientation of the surface layer is evaluated on the basis of the foregoing results of acoustic velocity changes.

The stress evaluation method of the invention is performed as follows.

The sensor 2 for transmitting and receiving a surface wave is moved to a position on the loaded portion where the stress to be evaluated exists (step 126), and then the acoustic velocity of the surface wave is measured at that position (step 127).

The difference between the acoustic velocity at the non-loaded portion described above and the acoustic velocity obtained at this loaded portion is calculated and stored in memory (step 128).

Next, similar to the case of the non-loaded portion, a propagational direction θ of the surface wave is compared with a preset angle $\theta_{max}$ (step 129). If the propagational direction θ is smaller than the preset angle $\theta_{max}$, the propagational direction of the surface wave is modified (step 130), and then the acoustic velocity of the surface wave is measured again.

If the propagational direction θ is greater than the preset angle $\theta_{max}$, the process advances to step 131 where the magnitude and direction of the stress are evaluated.

Figure 6:
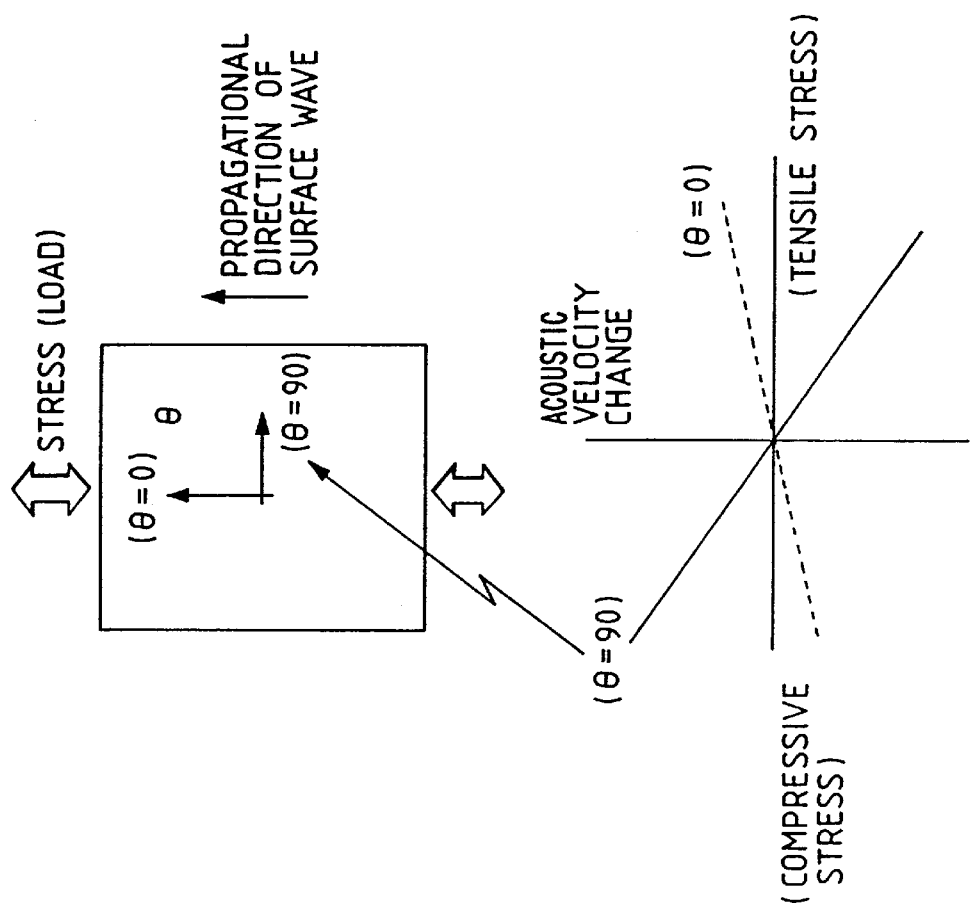
FIG. 6 is a schematic diagram showing a relationship between stress and the acoustic velocity change of the surface wave.

With reference to FIG. 6, a schematic diagram is shown which illustrates a relationship between an angle θ formed between the propagational direction of the surface wave and the direction of stress, and acoustic velocity changes of the surface wave.

Figure 17:
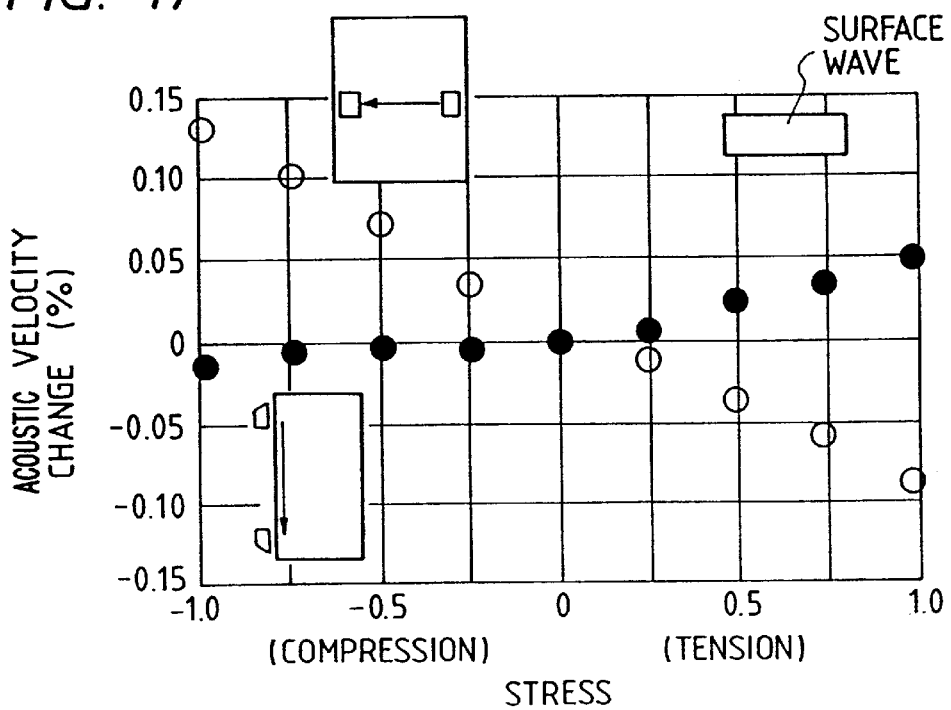
FIG. 17 is a diagram which shows a result of stress versus acoustic velocity changes of a surface wave in stainless steel.

FIG. 17 shows changes in surface wave acoustic velocity resulting in stainless steel when it is subjected to tensile and compressive stresses in uniaxial directions. A greater acoustic velocity change is observed when the surface wave is propagated perpendicular to the direction of the stress.

Since the change of acoustic velocity due to stress differs significantly depending on the propagational direction θ, the magnitude and direction of stress can be evaluated by measuring the acoustic velocity while varying the propagational direction θ.

Figure 7:
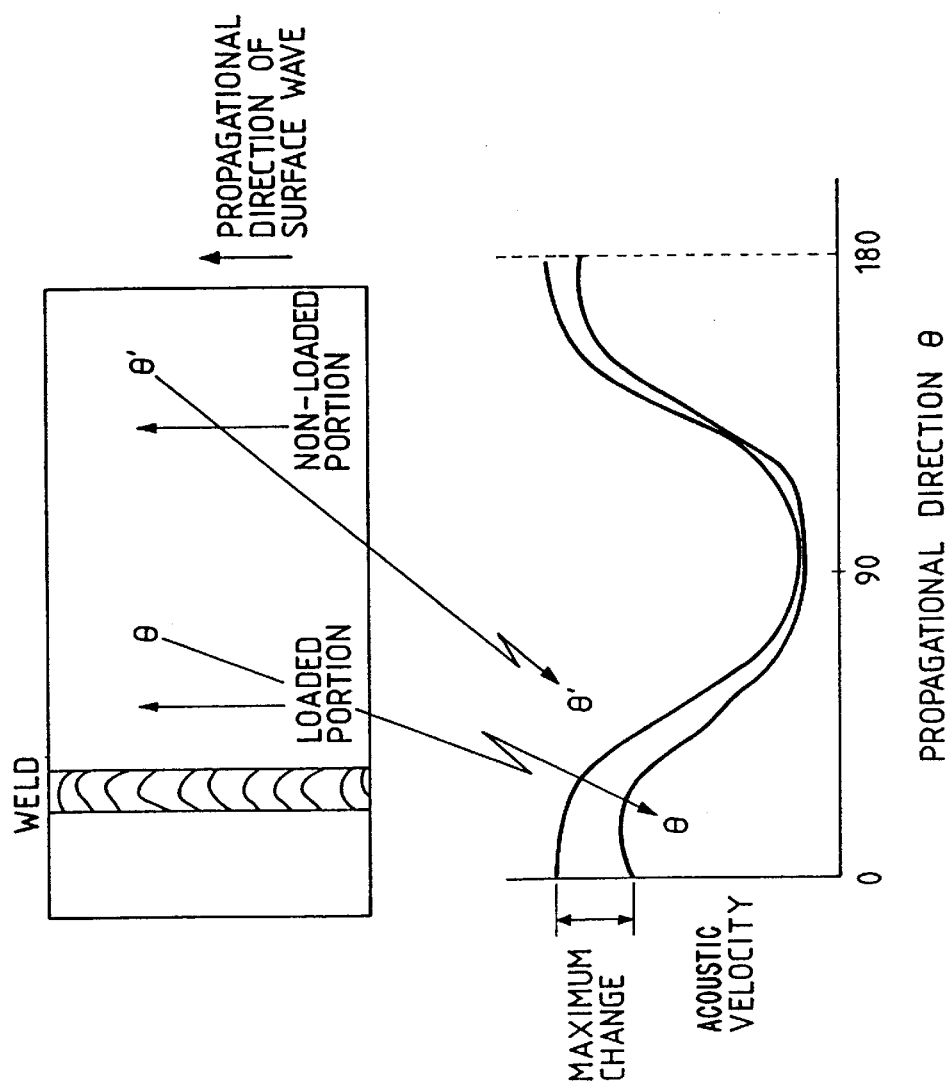
FIG. 7 is a schematic diagram illustrating a relationship between a propagational direction of the surface wave and a difference of its acoustic velocities between a loaded portion and a non-loaded portion.

Namely, with reference to FIG. 7, when a difference in acoustic velocity between the loaded portion and the non-loaded portion with respect to respective propagational directions is obtained, it becomes possible to evaluate the magnitude and direction of the stress, for example, from a maximum value of the acoustic velocity difference and the corresponding propagational direction θ yielding the maximum value.

Now, back to FIG. 3, therefore, in step 131, the magnitude and direction of stress are evaluated on the basis of the difference of acoustic velocity which was calculated in step 128.

Figure 4:
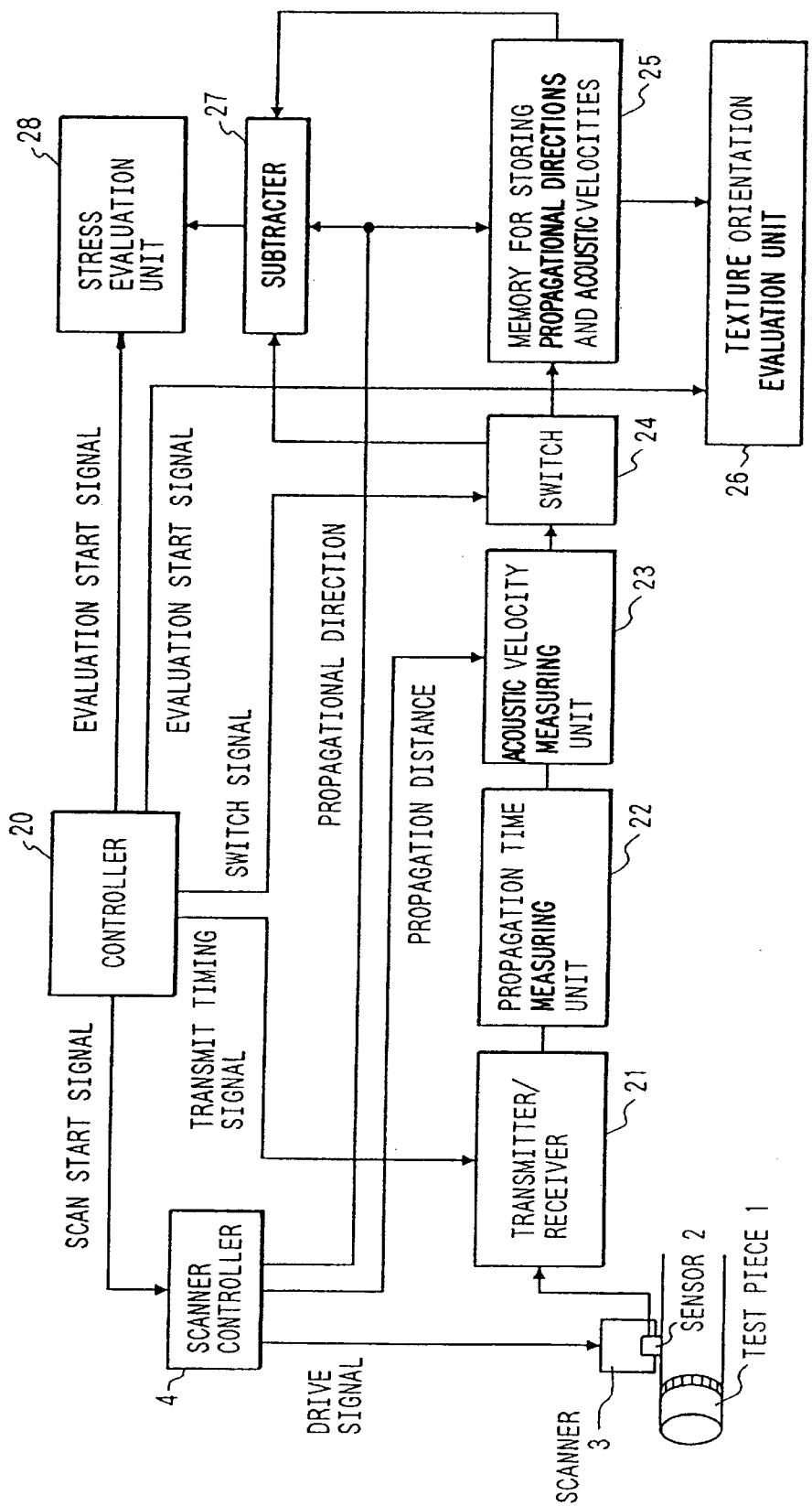
FIG. 4 is a schematic system diagram of an equipment configuration for implementing the stress evaluation method to evaluate stress in the surface layer according to FIG. 3.

FIG. 4 is a block diagram illustrative of one example of an equipment configuration for implementing the stress evaluation method for evaluating stress in the surface layer according to the method of FIG. 3.

At first, in response to a switch signal from a controller 20, a switch 24 connects an acoustic velocity measuring unit 23 and a propagational direction/acoustic velocity memory 25. In response to a drive signal from a scanner controller 4, a scanner 3 is actuated to place a sensor 2, which transmits and receives a surface wave, at a position on a non-loaded portion of a test piece 1.

Figure 19:
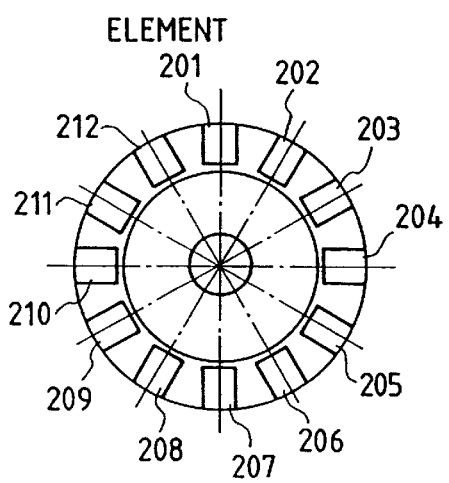
FIG. 19 is a plan view of an array sensor for a surface wave applicable in the embodiment of FIGS. 3 and 4.
Figure 20:
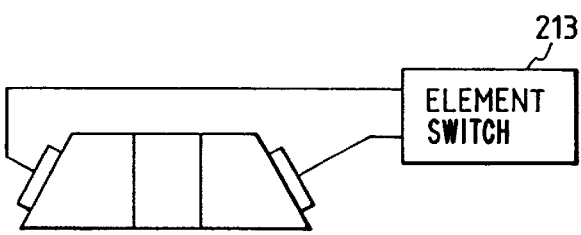
FIG. 20 is a longitudinal section of the array sensor of FIG. 19.

For sensor 2, an array sensor having twelve elements 201 to 212 disposed on a circumference of the test piece 1 as shown in FIG. 19 is used in which two elements disposed oppositely work as a pair to transmit a surface wave and receive it.

FIG. 19 shows an element switch 213 for switching between the twelve elements disposed circumferentially, such that, for example, element 201 is connected to a transmitter/receiver 21 as a transmitter and element 207 is connected thereto as a receiver.

Under such conditions, a surface wave is transmitted and received via the transmitter/receiver 21, and a surface wave signal corresponding to the received surface wave is sent from the transmitter/receiver 21 to a propagation time measuring unit 22.

The propagation time measuring unit 22 measures the propagation time for the surface wave to propagate through the surface layer of the test piece, and sends the result to acoustic velocity measuring unit 23.

The acoustic velocity measuring unit 23 obtains the acoustic velocity of the surface wave from a ratio between the propagation distance of the surface wave sent from the scanner controller 4 and the foregoing propagation time. The acoustic velocity thus obtained and the propagational direction of the surface wave sent from the scanner controller 4 are stored in the propagational direction/acoustic velocity memory 25.

The element switch 213 is caused to switch between elements in response to a signal from the controller 20 so as to vary the direction of the surface wave, repeating the foregoing steps until the propagational direction θ coincides with a preset angle $\theta_{max}$.

When the propagational direction θ becomes greater than the preset angle $\theta_{max}$, in response to an evaluation start signal issued from the controller 20, a texture orientation evaluation unit 26 evaluates the texture orientation in the test piece on the basis of a relationship between the propagational directions and acoustic velocities stored in the propagational direction/acoustic velocity memory 25.

Further, in response to a switch signal from the controller 20, the switch 24 connects the acoustic velocity measuring unit 23 and a subtracter 27. Further, in response to a drive signal from the scanner controller 4, the scanner 3 moves the sensor 2 to the loaded portion of the test piece 1.

Thereby, in the same manner as for the non-loaded portion, the acoustic velocity measuring unit 23 measures the acoustic velocity of the surface wave.

The subtracter 27 obtains the difference between the acoustic velocity at the loaded portion and the acoustic velocity at the non-loaded portion which has been stored in the propagational direction/acoustic velocity memory 25, and sends this difference of acoustic velocity and the corresponding propagational direction to a stress evaluation unit 28.

The stress evaluation unit 28 stores the propagational direction and the difference of acoustic velocity thus transmitted.

The propagational direction of the surface wave at the loaded portion is varied, and the acoustic velocity of the surface wave is measured once again. This series of operations is repeated until the propagational direction θ becomes greater than the preset angle $\theta_{max}$.

When the propagational direction θ becomes greater than the preset angle $\theta_{max}$, in response to an evaluation start signal from the controller 20, the stress evaluation unit 28 evaluates the magnitude of the stress and the direction thereof.

Figure 8:
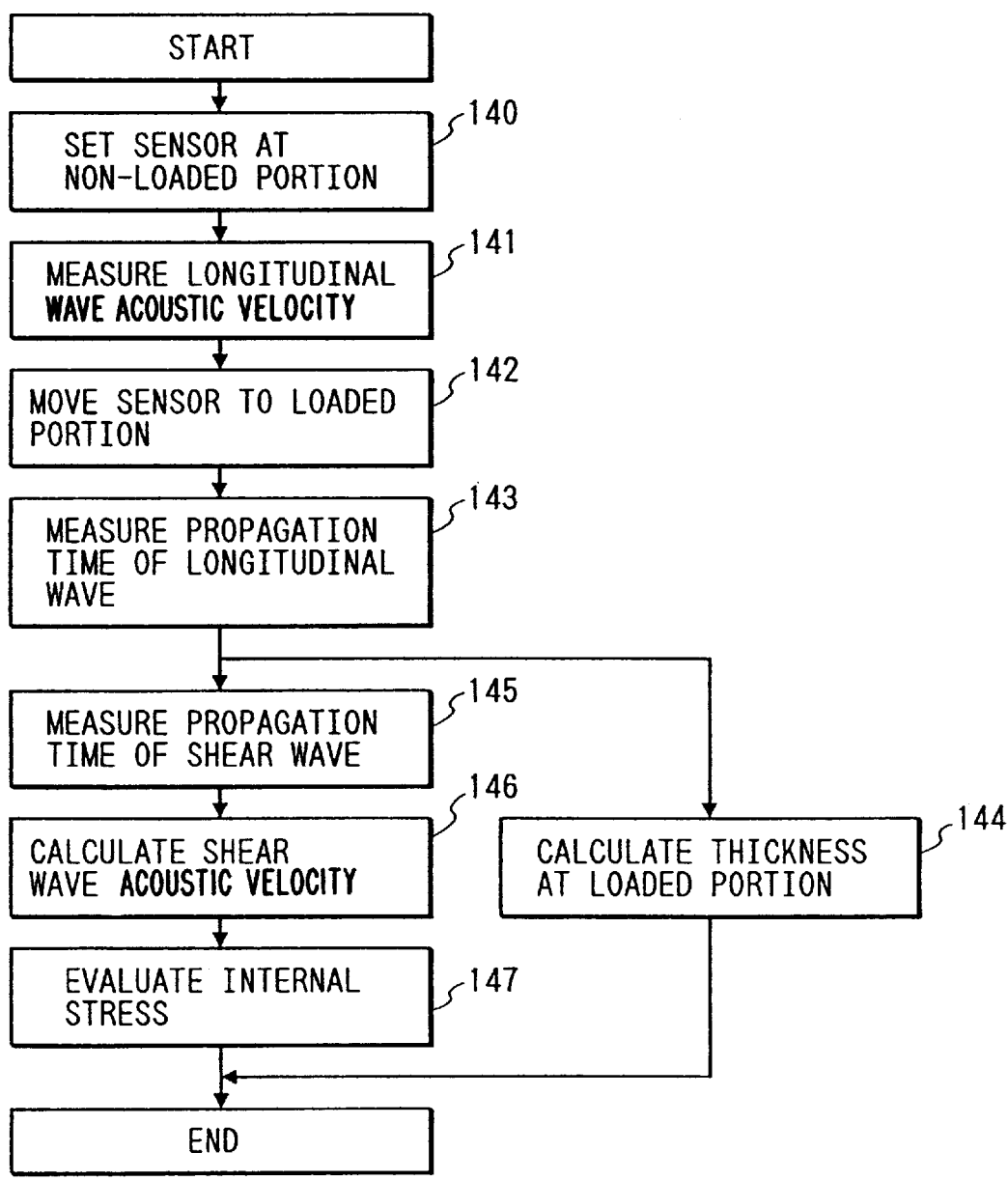
FIG. 8 is a flow chart of an internal average stress evaluation method of FIG. 1 for evaluating an internal average stress inside a test piece according to an embodiment of the invention.

FIG. 8 is a diagram showing an example of an average stress evaluation method for evaluating an internal average stress inside the test piece, as described in step 102 in FIG. 1.

The sensor 2 which transmits and receives a longitudinal wave or shear wave is placed at a position on the non-loaded portion of the test piece, the thickness of which is known (step 140 in FIG. 8).

Then, a longitudinal wave is transmitted into the test piece, and a reflected wave reflected from the bottom surface of the test piece is received to measure the acoustic velocity of the longitudinal wave thus transmitted (step 141).

Next, the sensor 2 is moved to a position on the loaded portion, the stress of which is desired to be evaluated and the thickness of which is unknown (step 142). At this position, a longitudinal wave is transmitted and received to measure the time for the longitudinal wave to propagate through the test piece (step 143).

After the step 143, the subsequent steps are divided into two paths: a path for calculating the thickness of the loaded portion and a path for evaluating the internal average stress.

Since the acoustic velocity V of an acoustic wave can be expressed as a ratio of the propagation distance and the propagation time, by using a wave reflected from the bottom surface of the test piece, and assuming that the thickness is H and the propagation time is t, then V is obtained by the following equation 1.

$$V = 2H/t \qquad \text{eq. 1}$$

In a loaded portion where stress is exerted, the test piece thickness changes by ΔH followed also by a change in the acoustic velocity itself.

Assuming a change in the propagation time due to a thickness change by ΔH to be Δt, and a change in the propagation time due to a stress change to be dt, the acoustic velocity $V_0$ at the loaded portion where stress is exerted is given by the following equation 2.

$$V_0 = 2(H+\Delta H)/(t+\Delta t+dt) \qquad \text{eq. 2}$$

Figure 10:
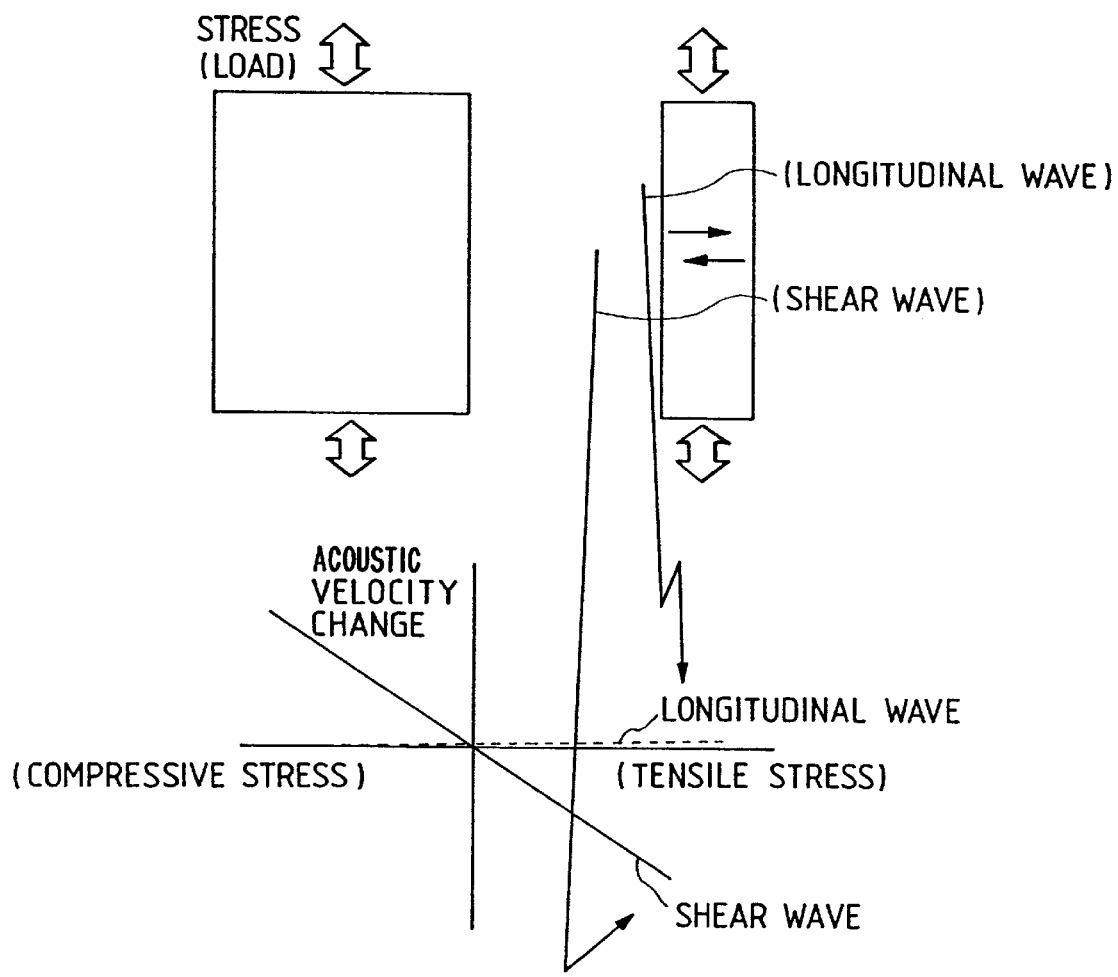
FIG. 10 is a schematic diagram illustrative of a relationship between stresses and acoustic velocity changes of a longitudinal wave and a shear wave.

On the other hand, while the acoustic velocity of the longitudinal wave changes little due to the stress change, as shown in FIG. 10, the acoustic velocity of the shear wave changes significantly due to the stress change.

Figure 18:
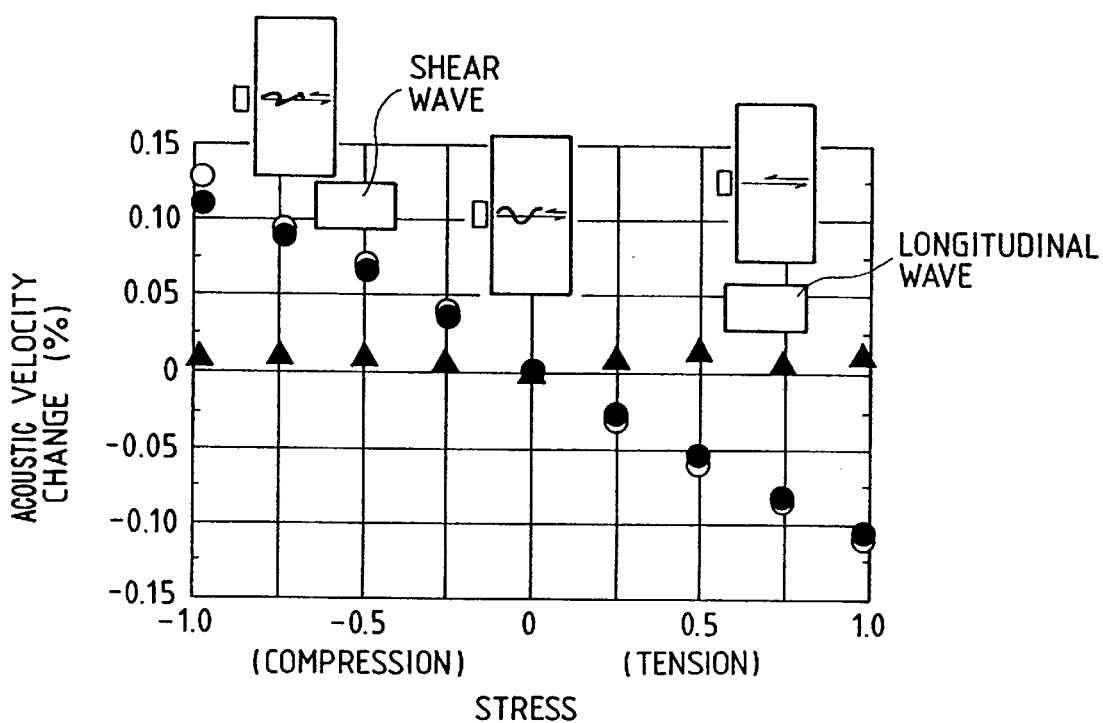
FIG. 18 is a diagram which illustrates a result of stress versus acoustic velocity changes of longitudinal and shear waves in stainless steel.

FIG. 18 shows a result of acoustic velocity changes of longitudinal waves and shear waves obtained for stainless steel when it was subjected to tensile and compressive stresses in uniaxial directions. It is clearly observed that the longitudinal wave acoustic velocity has changed little.

Figure 11:
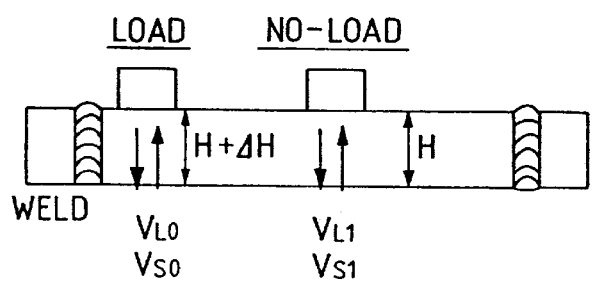
FIG. 11 is a schematic diagram illustrative of acoustic velocities of a longitudinal wave and a shear wave at a loaded portion and a non-loaded portion.

Therefore, assuming that acoustic velocities of longitudinal waves and shear waves at the non-loaded portion and the loaded portion are $VL_1$, $VL_0$, and $VS_1$, $VS_0$, respectively, as shown in FIG. 11, respective acoustic velocities at the loaded portion are given by the following equations 3 and 4.

$$VL_0 = 2(H+\Delta H)/(tL+\Delta tL+dtL) = 2(H+\Delta H)/TL_0 = VL_1 \qquad \text{eq. 3}$$

where dt≈0, $VL_1 = 2H/tL$.

$$VS_0 = 2(H+\Delta H)/(tS+\Delta tS+dtS) = 2(H+\Delta H)/TS_0 \qquad \text{eq. 4}$$

where Δt indicates a propagation time variation due to the thickness variation ΔH, and dt indicates a propagation time variation due to the stress change.

From the above two equations, and by assuming propagation times for the longitudinal wave and the shear wave in the loaded portion to be $TL_0$ and $TS_0$, a shear wave acoustic velocity can be obtained by the following equation 5.

$$VS_0 = (TL_0/TS_0)VL_1 \qquad \text{eq. 5}$$

In step 146, the thickness at the loaded portion can be evaluated by equation 3 using the longitudinal wave acoustic velocity $VL_1$, which was measured in step 141, and the longitudinal wave propagation time $TL_0$ at the loaded portion, which was measured in step 143.

Further, the process of evaluation of the internal average stress is as follows. In step 145, the propagation time $TS_0$ for the shear wave passing through the loaded portion is measured, then using the longitudinal wave acoustic velocity $VL_1$ which was measured in step 141 and the longitudinal wave propagation time $TL_0$ at the loaded portion which was measured in step 143, a shear wave acoustic velocity $VS_0$ is obtained by equation 5.

Finally, in step 147 of FIG. 8, on the basis of the relationship between the shear wave acoustic velocities and stresses obtained in advance, as shown in FIG. 10, a particular internal average stress corresponding to the shear wave acoustic velocity $VS_0$ obtained above can be evaluated.

Figure 9:
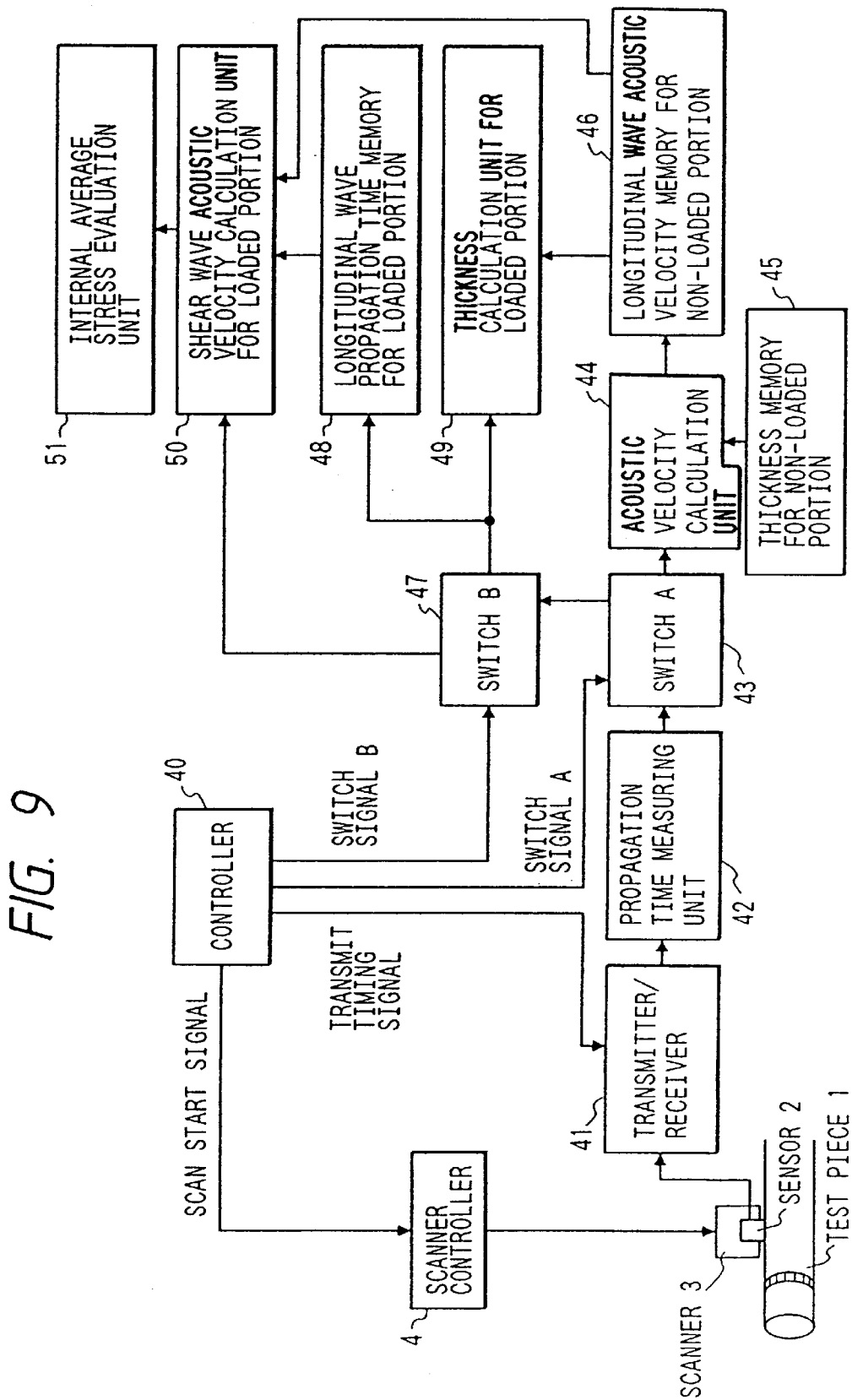
FIG. 9 is a schematic system diagram showing an equipment configuration for implementing the internal average stress evaluation method of FIG. 8.

With reference to FIG. 9, there is shown an example of an equipment configuration for implementing the internal average stress evaluation method of FIG. 8 according to the invention.

First, responsive to a switch signal A from a controller 40, a switch A 43 is caused to connect a propagation time measuring unit 42 and an acoustic velocity calculation unit 44. In response to a drive signal from a scanner controller 4, a scanner 3 is actuated to place a sensor which transmits and receives a longitudinal wave at a position on a non-loaded portion of a test piece 1.

Responsive to a signal from a transmitter/receiver 41, a longitudinal wave is transmitted and received, and then a received longitudinal wave signal is sent via the transmitter/receiver 41 to the propagation time measuring unit 42. The propagation time measuring unit 42 measures the time for the longitudinal wave to propagate through the test piece, and sends the result to the acoustic velocity calculation unit 44.

The acoustic velocity calculation unit 44 obtains the acoustic velocity of the longitudinal wave on the basis of data on a thickness at the non-loaded portion stored in a thickness memory 45 and the propagation time obtained above.

The acoustic velocity thus obtained is stored in a non-loaded portion longitudinal wave acoustic velocity memory 46. Then, in response to switch signals A and B from the controller 40, the switches A 43 and B 47 are switched to connect the propagation time measuring unit 42, a loaded portion thickness calculation unit 49 and a loaded portion longitudinal propagation time memory 48.

Further, in response to a drive signal from the scanner controller 4, the scanner 3 is actuated to move the sensor 2 to a loaded portion of the test piece 1.

Following the same sequence as for the non-loaded portion, the propagation time measuring unit 42 measures the propagation time for a longitudinal wave to propagate through the loaded portion.

The propagation time in the loaded portion obtained above is stored in the loaded portion longitudinal wave propagation time memory 48.

Further, the loaded portion thickness calculation unit 49 calculates the thickness of the loaded portion on the basis of the propagation time at the loaded portion and the longitudinal wave acoustic velocity at the non-loaded portion, which was stored in the non-loaded portion longitudinal wave acoustic velocity memory 46.

In response to a switch signal B from the controller 40, the switch B 47 is switched to connect the propagation time measuring unit 42 and a loaded portion shear wave acoustic velocity calculation unit 50.

In response to a signal from the transmitter/receiver 41, the sensor 2 transmits and receives a shear wave through the test piece, and then a received shear wave signal is transmitted via the transmitter/receiver 41 to the propagation time measuring unit 42.

The propagation time measuring unit 42 measures a time for the shear wave to propagate through the test piece, and sends the result to the loaded portion shear wave acoustic velocity calculation unit 50.

The loaded portion shear wave acoustic velocity calculation unit 50 calculates a shear wave acoustic velocity at the loaded portion on the basis of the shear wave propagation time measured above, the longitudinal wave propagation time which was stored in the loaded portion longitudinal propagation time memory 48 and the longitudinal wave acoustic velocity which was stored in the non-loaded portion longitudinal wave acoustic velocity memory 46, and then sends the calculated shear wave acoustic velocity to an internal average stress evaluation unit 51.

The internal average stress evaluation unit 51 evaluates an internal average stress based on the foregoing calculated shear wave acoustic velocity on the basis of the predetermined relationship between the shear wave acoustic velocities and the stresses.

Figure 12:
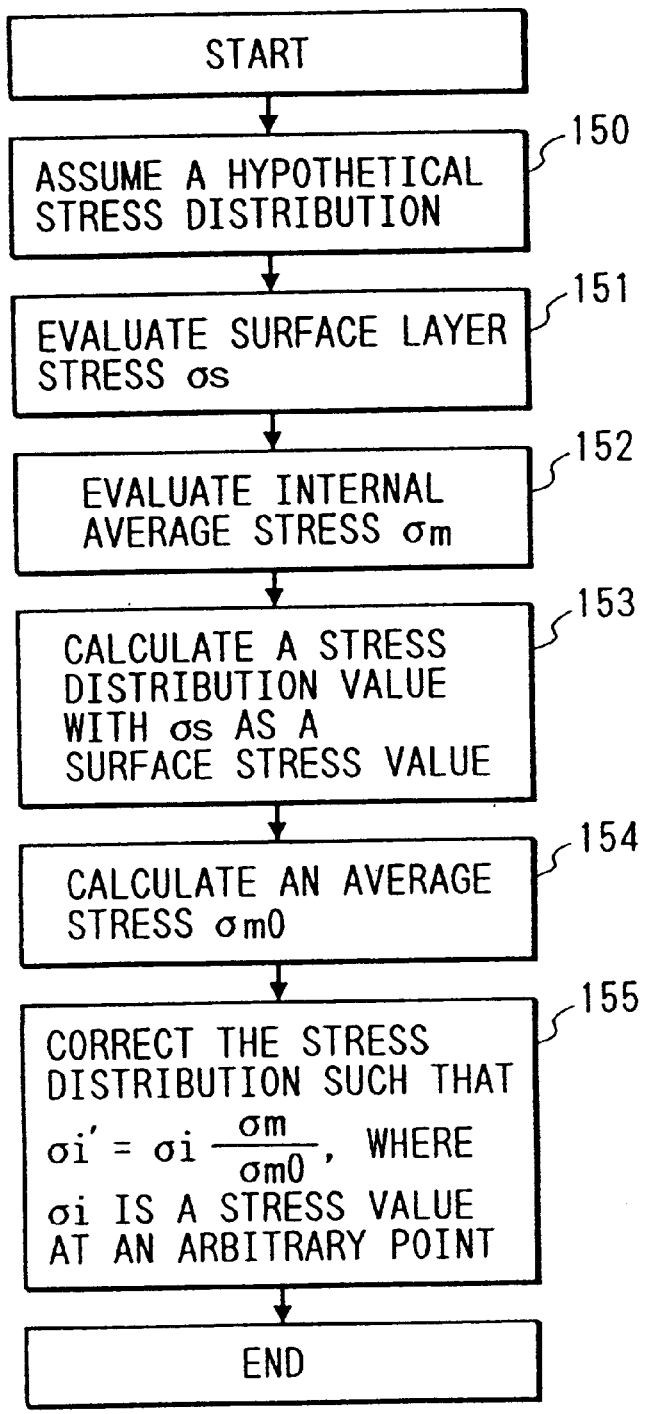
FIG. 12 is a flow chart of an internal stress distribution evaluation method of FIG. 1 for evaluating an internal stress distribution inside the test piece.

With reference to FIG. 12, there is shown a diagram illustrative of an example of an evaluation method for evaluating an internal stress distribution in the test piece as described in step 103 in FIG. 1.

A hypothetical stress distribution in the thickness direction at a loaded portion in the vicinity of a welded portion is obtained as a preliminary step by means of a strain gauge method or the like through destructive testing, and this hypothetical stress distribution is assumed to be a first approximation of the internal stress distribution (step 150).

Then, a surface layer stress as in the test piece is evaluated by the method described with reference to FIG. 3 (step 151), and an internal average stress am inside the test piece is evaluated by the method described with reference to FIG. 8 (step 152).

By assuming the foregoing surface layer stress as to be a surface stress value in the first approximation internal stress distribution, a respective stress value at each point in the stress distribution is obtained (step 153).

An average stress am0 in the thickness direction of the foregoing stress distribution is obtained by the following equation 6, by assuming the thickness direction to be on the y-axis (step 154).

$$\sigma m0 = \left( \int_0^{H+\Delta H} \sigma(y)\,dy \right) \Big/ (H + \Delta H) \qquad \text{eq. 6}$$

where (H+ΔH) is the thickness at the loaded portion. Finally, a stress value σi at each point i in the stress distribution is corrected by the following equation 7 thereby to obtain an internal stress distribution σi' (step 155).

$$\sigma i' = \sigma i \cdot (\sigma m/\sigma m0) \qquad \text{eq. 7}$$

Figure 13:
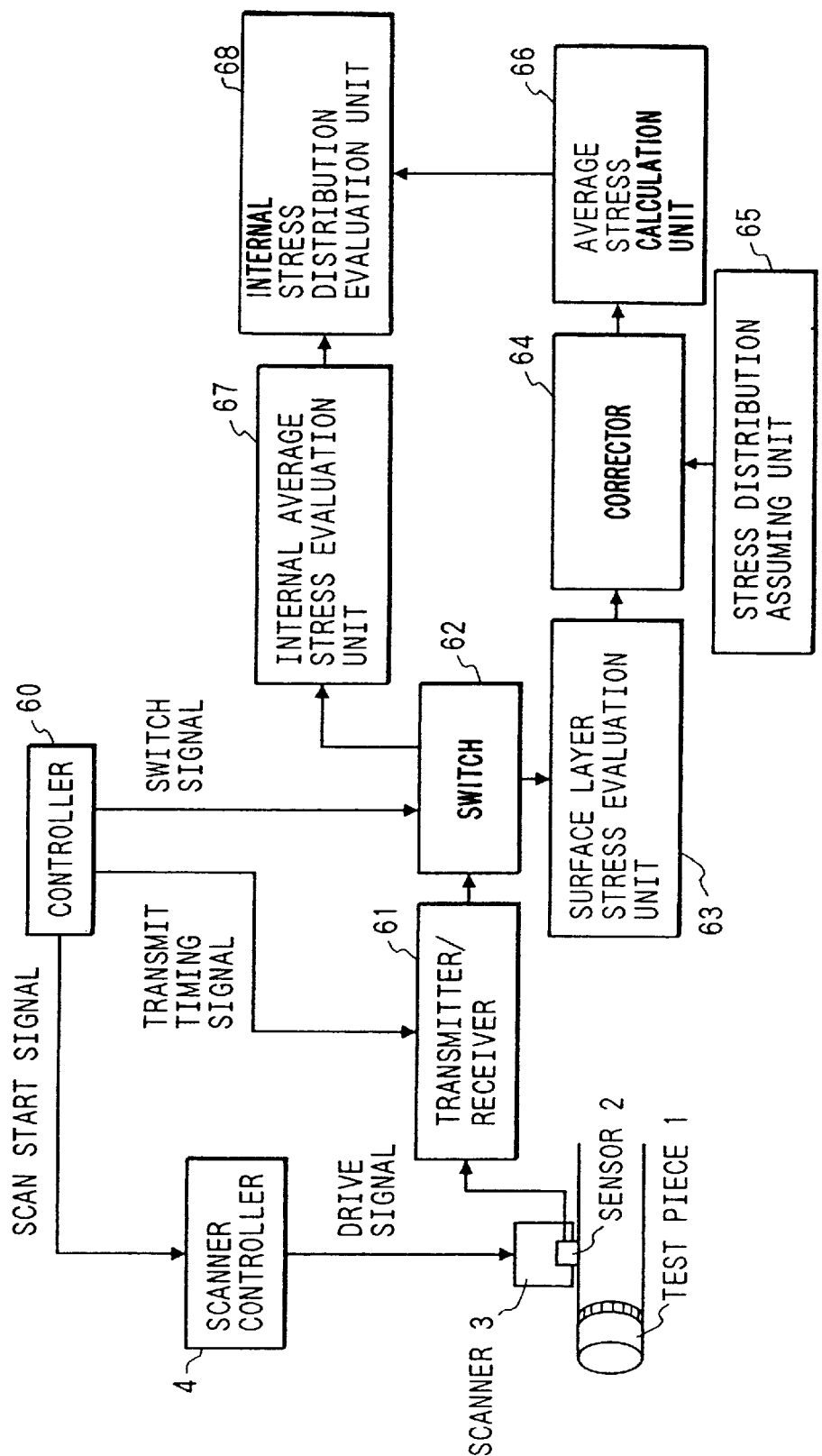
FIG. 13 is a system configuration for implementing the internal stress distribution evaluation method of FIG. 12.

With reference to FIG. 13 there is shown an example of an equipment configuration for implementing the internal stress distribution evaluation method described with reference to FIG. 12.

At first, in response to a switch signal from a controller 60, a switch 62 connects a transmitter/receiver 61 and a surface layer stress evaluation unit 63.

In response to a drive signal from a scanner controller 4, a sensor 2 which transmits and receives a surface wave is actuated by a scanner 3 to scan over a test piece 1.

Responsive to a signal from the transmitter/receiver 61, a surface wave is transmitted and received, and then a received surface wave signal is sent via the transmitter/receiver 61 to the surface layer stress evaluation unit 63.

The surface layer stress evaluation unit 63 evaluates the stress in the surface layer of the test piece based on the acoustic velocity of the surface wave, and sends the result to a corrector 64.

The corrector 64, by assuming that the surface layer stress which has been evaluated in the surface layer stress evaluation unit 63 is a surface stress value having a hypothetical stress distribution assumed in a stress distribution assuming unit 65, obtains a respective stress value at each point in the stress distribution, thereby correcting the stress distribution.

An average stress in the thickness direction of the aforementioned corrected stress distribution is obtained in an average stress calculation unit 66 operating in accordance with equation 6.

Then, in response to a switch signal from the controller 60, the switch 62 connects the transmitter/receiver 61 and an internal average stress evaluation unit 67.

In response to a drive signal from the scanner controller 4, the sensor 2 is adapted via the scanner 3 to scan over the test piece to transmit and receive a longitudinal wave and a shear wave.

On the basis of received signals of these longitudinal and shear waves, the internal average stress evaluation unit 67 evaluates an average stress in the thickness direction of the test piece.

An internal stress distribution evaluation unit 68, using an average stress amo which was calculated by the average stress calculation unit 66 and an average stress om which was evaluated by the internal average stress evaluation unit 67, obtains a stress value at each point from equation 7, and thereby evaluates an internal stress distribution.

Figure 14:
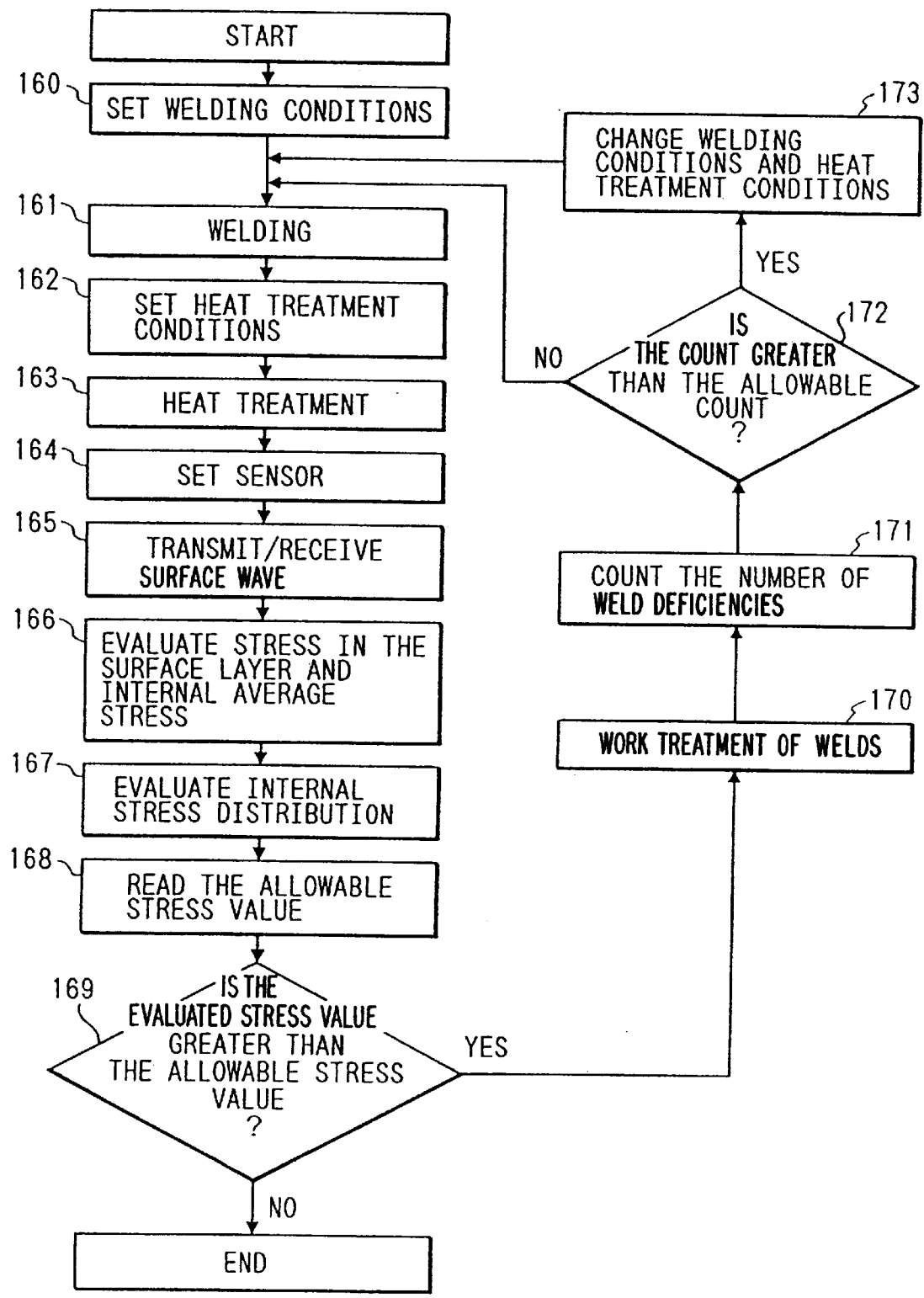
FIG. 14 is a flow chart illustrative of a welding procedure management method according to the invention.

FIG. 14 is a diagram illustrative of an example of a welding procedure management method using the stress evaluation method according to the invention.

Under preset welding conditions (step 160), stainless steel or the like is welded (step 161).

In order to improve the quality of the weld or to remove stress, appropriate heat treatment conditions are preset (step 162), and the welded stainless steel is heat treated under the preset heat conditions (step 163).

After heat treatment, an acoustic transmitter/receiver sensor is disposed at a target point (step 164) to transmit and receive a surface wave (step 165).

Then, based on the acoustic velocity of the surface wave, the surface layer stress and the internal average stress in the test piece are evaluated (step 166). By using the evaluated surface layer stress value and the internal average stress value, and through correction of the assumed internal stress distribution, an internal stress distribution is evaluated (step 167).

Then, an allowable stress value which has been predetermined and stored in view of the material strength, design margins and the like is read (step 168).

Upon comparison of the foregoing evaluated stress value with the allowable stress value (step 169), if the evaluated stress value is smaller, it is judged that the welding and heat treatment conditions are adequate, thereby ensuring the reliability of the weld and base metal, and the procedure is ended.

However, if the evaluated stress value is larger than the allowable stress value, it is judged that there exists some weld deficiency, and the welded portion is work treated (step 170).

The number of weld deficiencies is counted (step 171), and the count is compared with a preset allowable count (172).

If the number of weld deficiencies counted is smaller than the preset allowable count, the welded portion is subjected to rewelding and heat treatment under the initial welding and heat treatment conditions.

If the number of weld deficiencies counted is greater than the preset allowable count, the welding and heat treatment conditions are modified so as to be different from the initial welding and heat treatment conditions (step 173).

Then, the welded portion is subjected to rewelding and heat treatment under the modified welding and heat treatment conditions.

Although both the welding conditions and the heat treatment conditions are changed at the same time in the above embodiment, the invention is not limited thereto, and either one of the welding conditions and the heat treatment conditions may be changed to attain the same effect of the invention.

Figure 15:
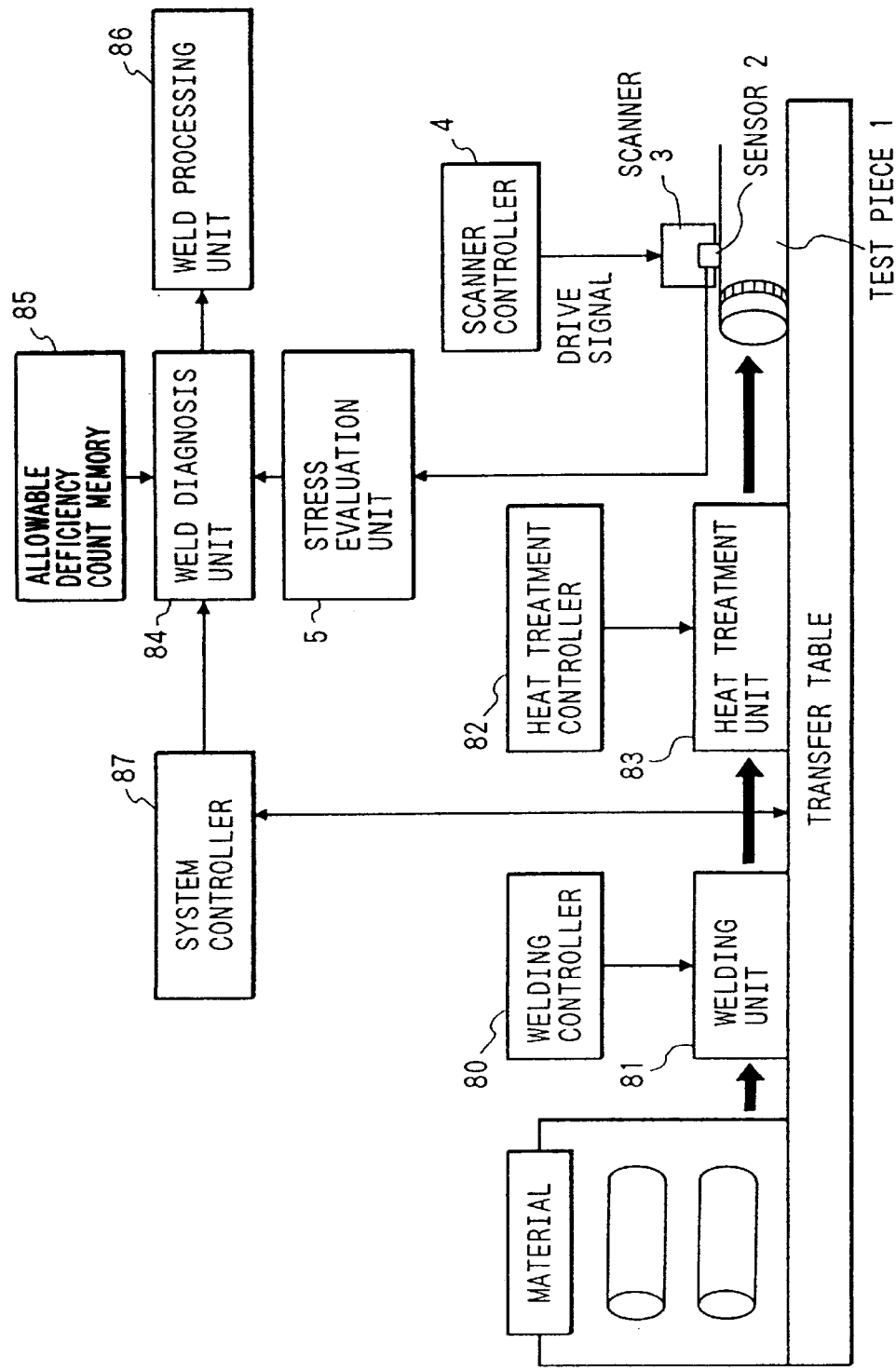
FIG. 15 is a system configuration for implementing the welding procedure management method of FIG. 14.

FIG. 15 is a diagram illustrative of one example of an equipment arrangement for implementing the welding procedure management method of FIG. 14 according to the invention. Numeral 1 designates a test piece which is a piping or the like for use in a power generating plant or the like.

The test pipe is welded by a welder 81 according to welding conditions prescribed and set in a welding controller 80.

Then, the welded test piece is moved to a heat treatment unit 83 to be subjected to a heat treatment according to heat treatment conditions prescribed and set in a heat treatment controller 82.

Then, in response to a drive signal from a scanner controller 4, a scanner 3 is actuated to place a sensor 2 which transmits and receives acoustic waves including a surface wave, a longitudinal wave, and a shear wave at a target position on the test piece.

In response to a signal from a stress evaluation unit 5, the sensor transmits and receives acoustic waves including a surface wave, a longitudinal wave, and a shear wave, and then, based on received acoustic wave signals, the stress evaluation unit 5 evaluates a surface layer stress, an internal average stress and an internal stress distribution in the test piece.

The value of stress thus evaluated is sent to a weld diagnosis unit 84.

The weld diagnosis unit 84 reads out an allowable stress value stored in an allowable value memory 85, which is compared with the evaluated stress value to verify the reliability of the weld of the test piece.

When the weld and base metal are judged to be sound and normal, the welding management procedure is completed.

If, however, any weld deficiencies are judged to be present, a weld processing unit 86 is adapted to apply work processing to the weld.

Further, the weld diagnosis unit 84 is adapted to count the number of weld deficiencies, and compares the number of weld deficiencies actually counted and an allowable deficiency count stored in an allowable deficiency count memory 85.

If the weld deficiency count is smaller than the allowable deficiency count, the test piece is subjected to rewelding and heat treatment under the same welding and heat treatment conditions as initially set.

On the other hand, if the weld deficiency count is larger than the allowable deficiency count, the test piece is subjected to rewelding and heat treatment under modified welding and heat treatment conditions.

A system controller 87 controls the timings of transfer of the test piece 1, operation of each piece of equipment and the like.

The advantages of the invention which have been described hereinabove will be summarized as follows.

According to the invention, precision of stress evaluation in the surface layer of the test piece can be improved advantageously and significantly since any influence due to the texture orientation of the surface layer in the test piece can be minimized.

According to the invention, a precise average stress evaluation can be advantageously accomplished even in a test piece having an unknown thickness since a longitudinal wave is utilized which enables the evaluation of the thickness of the test piece by minimizing the influence of stress exerted therein.

According to the invention, a stress distribution in the thickness direction of the test piece can be evaluated precisely because of the high precision stress evaluation accomplished above.

According to the invention, since diagnosis of the equipment and plant is conducted through comparison of the result of a high precision stress evaluation and a preset allowable stress value, reliability of the diagnosis can be substantially improved.

According to the invention, since, in addition to the advantage mentioned above, the modes of material degradation of the test piece can be accumulated over time and can be reflected in the stress evaluation, the reliability of diagnosis of the equipment and plant can be further improved.

According to the invention, reliability of the weld and base metal can be advantageously and significantly improved by a high precision stress evaluation made available.

According to the invention, in addition to the advantage mentioned above, since the initial welding and heat treatment conditions are normally set at their best conditions, if rewelding is required, rewelding and heat treatment are performed under the initial welding and heat treatment conditions in an attempt to provide the best welding and heat treatment conditions therefor, such that the reliability of the weld and base metal can be improved substantially.

According to the invention, in addition to the advantage mentioned above, if the initial welding and heat treatment conditions are not adequate to overcome the deficiencies, it is possible to modify the initial welding and heat treatment conditions such that a high quality weld and base metal can be provided.

Still further, according to the invention, it is possible to provide an apparatus which is capable of accomplishing the same advantages as those mentioned above.

What is claimed is:

1. A stress evaluation method for evaluating stress acting on a test piece to be tested from changes in an acoustic velocity of an acoustic wave which propagates through said test piece, wherein the stress evaluation method comprises the steps of:

changing a propagational direction of a surface wave which propagates in a surface layer of said test piece both at a non-loaded portion and a loaded portion of the test piece;

measuring an acoustic velocity of said surface wave; and evaluating stress at the loaded portion of said test piece based on a difference in acoustic velocities of said surface wave between the non-loaded portion and the loaded portion of said test piece.

2. A diagnosis method for diagnosing a test piece to be tested comprising the steps of:

evaluating stress in the test piece by means of the stress evaluation method according to claim 1 to obtain an evaluated stress value; and comparing the evaluated stress value with a predetermined allowable stress value.

3. A diagnosis method for diagnosing a test piece to be tested according to claim 2, further comprising the steps of:

repeating the step of evaluating stress in the test piece if the evaluated stress value is smaller than the predetermined allowable stress value; and identifying a mode of material degradation in the test piece based on time variations of said evaluated stress value.

4. A welding procedure management method comprising the steps of:

evaluating residual stress in a test piece which has been subjected to a first welding and heat treatment by the stress evaluation method according to claim 1 to obtain an evaluated residual stress value; and applying a second welding and heat treatment process to the test piece if said evaluated residual stress value is greater than a predetermined allowable residual stress value.

5. The welding procedure management method according to claim 4, wherein conditions of the second welding and heat treatment process are the same as conditions of the first welding and heat treatment process.

6. The welding procedure management method according to claim 5, further comprising the steps of:

reevaluating a residual stress in the test piece which has been subjected to the second welding and heat treatment process by repeating the step of evaluating residual stress in the test piece to obtain a reevaluated residual stress value;

applying to the test piece a third welding and heat treatment process having conditions which are different from the conditions of the first and second welding and heat treatment processes if said reevaluated residual stress is greater than said predetermined allowable residual stress value; and repeating the step of evaluating residual stress in the test piece.

7. The welding procedure management method according to claim 4, wherein conditions of the second welding and heat treatment process are different from conditions of said first welding and heat treatment process.

8. A stress evaluation apparatus having acoustic wave propagation means for propagating an acoustic wave through a test piece to be inspected, receiver means for receiving an acoustic wave which has propagated through said test piece, and means for evaluating stress in said test piece in response to an acoustic wave received at said receiver means and based on a change in an acoustic velocity of said acoustic wave propagating through said test piece, wherein the stress evaluation apparatus comprises:

acoustic wave propagation direction varying means for variably changing a propagational direction of a surface wave propagating through a surface layer of said test piece under inspection both at a non-loaded portion and a loaded portion of said test piece;

acoustic velocity measuring means for measuring an acoustic velocity of said surface wave; and stress evaluation means for evaluating stress at said loaded portion of said test piece based on a difference in acoustic velocity of said surface wave both at said non-loaded portion and said loaded portion of said test piece.

9. The stress evaluation method according to claim 1, wherein the stress evaluated at the loaded portion of the test piece is a surface stress in the surface layer of the test piece at the loaded portion of the test piece.

10. The stress evaluation apparatus according to claim 8, wherein the stress evaluated at the loaded portion of the test piece is a surface stress in the surface layer of the test piece at the loaded portion of the test piece.

* * * * *